(12) United States Patent
Corndorf et al.

(10) Patent No.: US 8,145,320 B2
(45) Date of Patent: Mar. 27, 2012

(54) TELEMETRY CONTROL FOR IMPLANTABLE MEDICAL DEVICES

(75) Inventors: Eric D. Corndorf, Minneapolis, MN (US); Lucas J. J. M. Meekes, Velp (NL)

(73) Assignee: Medtronic, Inc., Minneapolis ( * ) Notice: Subject to any disclaimer, the term of this patent is extended or adjusted under 35 U.S.C. 154(b) by 540 days.

(21) Appl. No.: 12/144,158

(22) Filed: Jun. 23, 2008

(65) Prior Publication Data

US 2009/0248115 A1    Oct. 1, 2009

Related U.S. Application Data

(60) Provisional application No. 61/039,667, filed on Mar. 26, 2008.

(51) Int. Cl.
*A61N 1/08* (2006.01)
(52) U.S. Cl. ............................................ 607/60; 607/32
(58) Field of Classification Search .............. 607/30–32, 607/59, 60
See application file for complete search history.

(56) References Cited

U.S. PATENT DOCUMENTS

| | | | |
|---|---|---|---|
| 4,545,380 A | 10/1985 | Schroeppel | |
| 4,846,195 A | 7/1989 | Alt | |
| 5,276,680 A * | 1/1994 | Messenger | 370/311 |
| 5,304,206 A | 4/1994 | Baker, Jr. et al. | |
| 5,552,645 A | 9/1996 | Weng | |
| 5,620,475 A | 4/1997 | Magnusson | |
| 5,792,205 A | 8/1998 | Alt et al. | |
| 6,080,187 A | 6/2000 | Alt et al. | |
| 6,482,154 B1 | 11/2002 | Haubrich et al. | |
| 6,647,298 B2 * | 11/2003 | Abrahamson et al. | 607/6 |
| 6,985,773 B2 | 1/2006 | Von Arx et al. | |
| 2003/0114898 A1 | 6/2003 | Von Arx et al. | |
| 2003/0149459 A1 | 8/2003 | Von Arx et al. | |
| 2005/0113885 A1 | 5/2005 | Haubrich et al. | |
| 2006/0229053 A1 | 10/2006 | Sivard | |
| 2007/0167993 A1 | 7/2007 | Dudding et al. | |
| 2008/0071328 A1 | 3/2008 | Haubrich et al. | |

OTHER PUBLICATIONS

International Search Report, PCT/US2009/036651, 4 pages.

* cited by examiner

*Primary Examiner* — Michael Kahelin
(74) *Attorney, Agent, or Firm* — Stephen W. Bauer; Michael J. Ostrom (57) ABSTRACT

An implantable medical device (IMD) and method are provided in which a telemetry module in the IMD includes a configurable polling interval at which the telemetry module is powered up from a low power inactive state to perform sniff operations for detecting whether communication signals are being received from an external device. The IMD includes at least one sensor for sensing at least one parameter, a controller receiving data from the sensor, and the telemetry module coupled to the controller for facilitating communication between the IMD and an external device. The polling interval of the telemetry module is configured based upon the parameter(s) sensed by the sensor, such that the polling interval is configured to conserve power consumption of the IMD. The polling interval is either decreased or increased to respectively increase or decrease the frequency of the sniff operations based on the parameters sensed at the IMD.

19 Claims, 6 Drawing Sheets

Wakeup Polling Interval

TELEMETRY CONTROL FOR IMPLANTABLE MEDICAL DEVICES

RELATED APPLICATIONS

This application claims the benefit of and priority to U.S. Provisional Application Ser. No. 61/039,667, filed Mar. 26, 2008, entitled, "Telemetry Control for Implantable Medical Devices," the contents of which are incorporated by reference herein in its entirety.

TECHNICAL FIELD

This disclosure relates generally to implantable medical devices (IMDs) and more particularly to IMDs capable of telemetry.

BACKGROUND

A wide variety of IMDs have been developed in order to monitor patient conditions and deliver therapy to the patient. An IMD typically includes a hermetically sealed housing coupled to one or more leads that are surgically implanted inside a patient for sensing conditions or for administering therapy. The IMD may provide therapeutic stimulation to the patient or may deliver drugs or agents to the patient. Alternatively or additionally, the IMD may have sensing or monitoring capabilities. For example, the IMD may sense information within a patient and store the sensed information for subsequent analysis. In some cases, the sensed information may be used directly by the IMD to adjust or control the therapy that is delivered to the patent. Telemetry is used to communicate sensed information from the IMD to an external medical device so that analysis of the sensed information can be performed. Telemetry is further used to communicate information or instructions from external medical devices to the IMD. The IMD includes a telemetry module for performing such telemetry.

In order to perform telemetry communications with an external medical device, the telemetry module in the IMD can be programmed to perform so called "sniff" operations in which the telemetry module senses received signals to determine whether other devices are trying to communicate or are available to communicate with the IMD. The signals received by the telemetry module during these sniff operations are referred to as wake-up signals that direct the IMD to power on various components to communicate with the external medical device.

SUMMARY

In one or more embodiments, an implantable medical device (IMD) and method are provided in which a telemetry module in the IMD is normally maintained in a low power inactive "sleep" state and powered up to perform sniff operations according to a configurable polling interval. The polling interval is the time interval in between sniff operations at which the telemetry module is powered up to sense communication signals being received from an external device. The IMD includes at least one sensor configured to sense at least one parameter, a controller receiving data from the sensor, and a telemetry module coupled to the controller for facilitating communication between the IMD and an external device. The telemetry module possesses a configurable polling interval at which the telemetry module is activated for a period of time to perform sniff operations to detect whether a communication signal is being received from an external device. The polling interval of the telemetry module is configured at least partially based upon the at least one parameter sensed by the sensor(s). If a communication signal from an external device is sensed during these sniff operations, the IMD will become aware that other external devices are either attempting to communicate with the IMD or are within telemetry range capable of communicating with the IMD.

In one or more embodiments, the telemetry module is configured to operate in a low power inactive mode until the telemetry module is activated according to the polling interval, wherein the telemetry module is configured to adjust a length of the polling interval based upon the parameter(s) sensed by the sensor(s). In one embodiment, the sensor is a motion sensor. In one embodiment, the sensor is configured to sense an activating motion (e.g., a tapping motion imparted on the IMD by the patient, a physician or another individual). In one embodiment, the sensor is a position sensor. In one embodiment, the sensor is a patient activity sensor. In one embodiment, the sensor is configured to sense a condition of the patent in which the IMD is implanted. In one embodiment, the sensor is configured to sense magnetic or inductive coupling or other near-field telemetry signals.

In one or more embodiments, the telemetry module is configured to reduce a length of the polling interval of the telemetry module in response to the parameter sensed by the sensor. For example, the polling interval can be reduced to zero such that the telemetry module is immediately activated to perform sniff operations in response to the sensed parameter (e.g., when patient movement or tapping is sensed). In one or more embodiments, the length of the polling interval of the telemetry module can be increased in response to the parameter sensed by the sensor (e.g., when the patient is sleeping or no movement is sensed). In one or more embodiments, the telemetry module is configured to reduce the length of the polling interval at a greater rate than the polling interval is increased.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

Since the battery capacity in an IMD is very limited, the power consumed by the components of the IMD can be conserved by keeping the components in a power off or low power "sleep" state when they are not being utilized. The present disclosure describes an implantable medical device (IMD) and a method for operating the same in which a polling interval of a telemetry module in the IMD is configured so as to conserve power consumption of the IMD. In the following description, numerous embodiments are set forth in order to provide a thorough understanding of the invention. It will be apparent, however, to one skilled in the art, that these and other embodiments may be practiced without these specific details. In some instances, features well-known to those skilled in the art have not been described in detail in order not to obscure the present disclosure.

Figure 1:
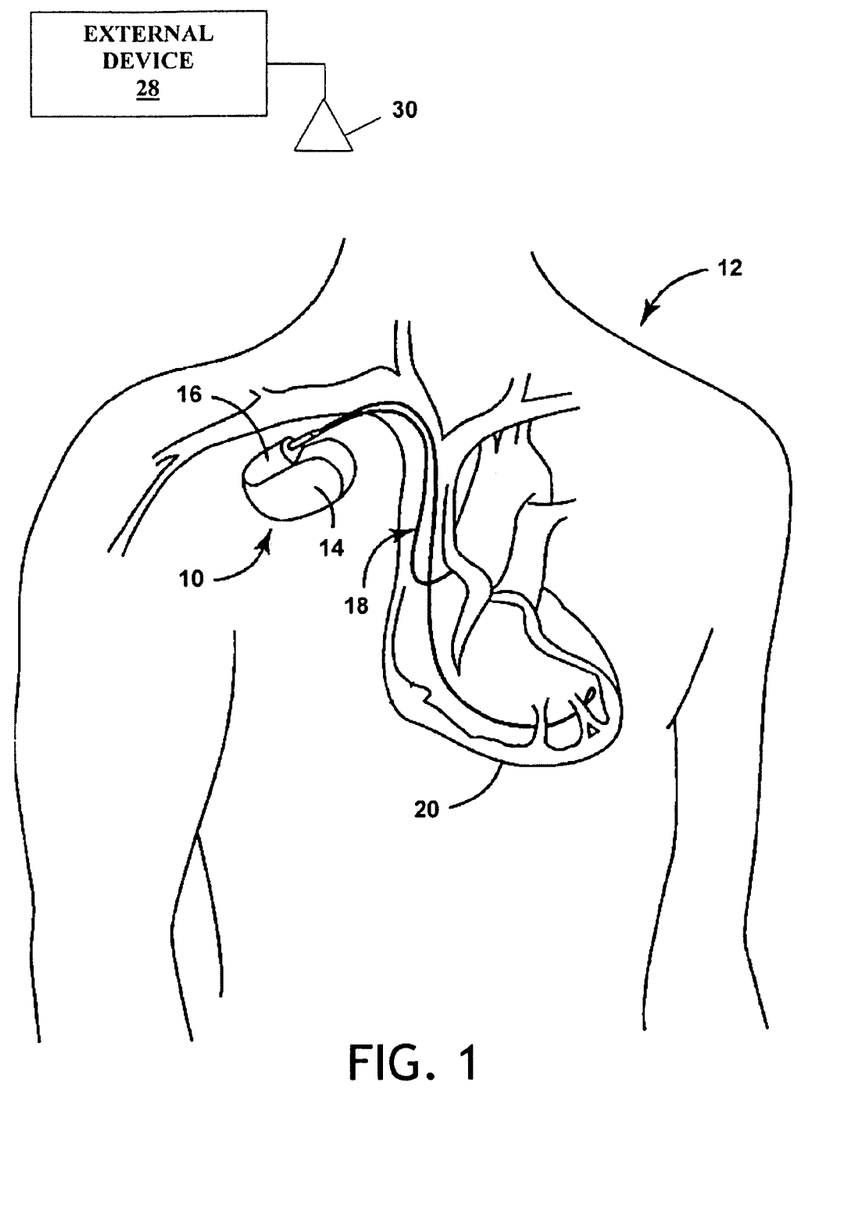
FIG. 1 illustrates an implantable medical device system in accordance with an embodiment of the present disclosure implanted in a human body.

FIG. 1 is a simplified schematic view of one embodiment of implantable medical device ("IMD") 10 of the present disclosure implanted within a human body 12. IMD 10 comprises a hermetically sealed enclosure 14 and connector module 16 for coupling IMD 10 to electrical leads 18 arranged within body 12, such as pacing and sensing leads 18 connected to portions of a heart 20 for delivery of pacing pulses to a patient's heart 20 and sensing of heart 20 conditions. While IMD 10 is depicted in a pacemaker device configuration in FIG. 1, it is understood that IMD 10 may comprise any type of implanted device including, but not limited to implantable cardioverter-defibrillators (ICDs), an implantable combination pacemaker-cardioverter-defibrillator (PCDs), implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Figure 2:
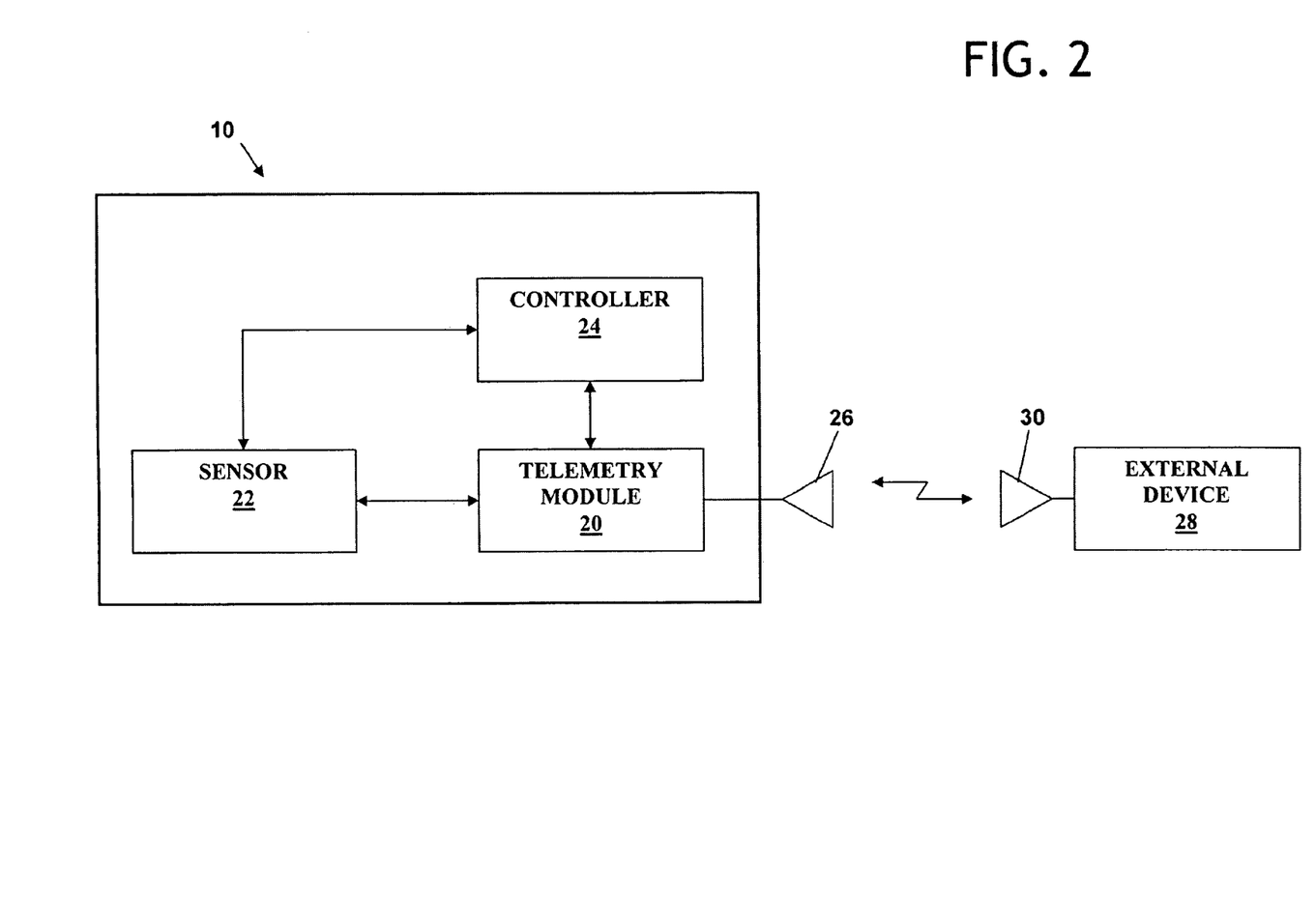
FIG. 2 is a block diagram illustrating the various components of one embodiment of an implantable medical device configured to operate in accordance with the present disclosure.

FIG. 2 is a block diagram illustrating the constituent components of IMD 10 in accordance with one embodiment having a microprocessor-based architecture. IMD 10 is shown as including telemetry module 20, at least one sensor 22, and controller 24.

Telemetry module 20 may comprise any unit capable of facilitating wireless data transfer between IMD 10 and an external device 28, where external device 28 may comprise an external medical device, a programming device, a remote telemetry station, a physician-activated device, a patient-activated device, a display device or any other type of device capable of sending and receiving signals to and from IMD 10. Telemetry module 20 and external device 28 are respectively coupled to antennas 26 and 30 for facilitating the wireless data transfer. Telemetry module 20 may be configured to perform any type of wireless communication. For example, telemetry module 20 may send and receive radio frequency (RF) signals, infrared (IR) frequency signals, or other electromagnetic signals. Any of a variety of modulation techniques may be used to modulate data on a respective electromagnetic carrier wave. Alternatively, telemetry module 20 may use sound waves for communicating data, or may use the patient's tissue as the transmission medium for communicating with a programmer positioned on the patients skin. In any event, telemetry module 20 facilitates wireless data transfer between IMD 10 and external device 28.

Controller 24 may comprise any of a wide variety of hardware or software configurations capable of executing algorithms to utilize data received from sensor 22 and configure the polling interval of telemetry module 20. Example hardware implementations of controller 24 include implementations within an application specific integrated circuit (ASIC), a field programmable gate array (FPGA), a programmable logic device, specifically designed hardware components, one or more processors, or any combination thereof. If implemented in software, a computer readable medium, such as a memory in the IMD 10, may store computer readable instructions, e.g., program code, that can be executed by controller 24 to carry out one of more of the techniques described herein. For example, the memory may comprise random access memory (RAM), read-only memory (ROM), non-volatile random access memory (NVRAM), electrically erasable programmable read-only memory (EEPROM), flash memory, or the like. Telemetry module 20 may likewise comprise any of a wide variety of the above-listed hardware or software configurations capable of executing algorithms for facilitating wireless telemetry.

IMDs typically must rely entirely on an implanted power source. It is desirous to keep the physical size of an IMD to a minimum, which further places limitations on the size of the implanted power source. The various components of IMD 10 (i.e., sensor 22, telemetry module 20, controller 24) rely on the power source for power. For embodiments of IMD 10 that have nonrechargeable batteries, IMD 10 must be surgically replaced when the power source is fully depleted. For embodiments of IMD 10 having rechargeable batteries, a surgical procedure is not required when the power source is depleted, however, the power source must be recharged more frequently since it cannot store as much energy. Thus, power conservation is particularly important in IMD 10. Further, consistently powering up telemetry module 20 to perform sniff operations require electrical power which can drain the battery (now shown) of IMD 10 at an unacceptable rate.

In one or more embodiments, IMD 10 and a method for operating the same is provided in which telemetry module 20 is normally maintained in a power off or low power inactive "sleep" state in order to conserve power. Telemetry module 20 is only powered up to perform actual telemetry operations and/or to perform sniff operations in which telemetry module 20 is powered up to detect communication signals being received from an external device 28. If a communication signal from an external device 28 is detected during these sniff operations, it is determined that external device 28 is either attempting to communicate with IMD 10 or external device 28 is within telemetry range capable of communicating with IMD 10 (e.g., external device 28 is transmitting beacon signals that are being received by IMD 10). IMD 10 can then power up ("wake up") the necessary components required to transmit or receive data from external device 28.

Figure 3A:
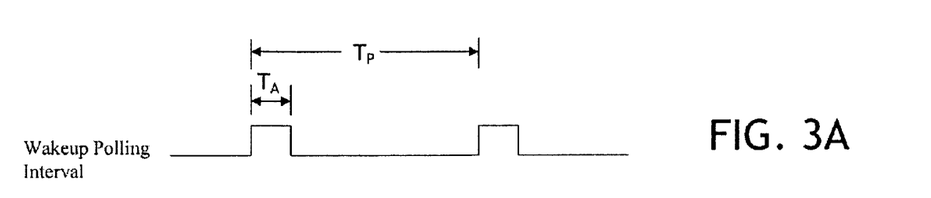
FIGS. 3A-3C are illustrations of various wakeup polling intervals for the telemetry module according to differing conditions in accordance with embodiments of the implantable medical device of the present disclosure.

Since consistently powering up telemetry module 20 to perform such sniff operations requires electrical power which can drain the power source of IMD 10 at an unacceptable rate, in one or more embodiments, telemetry module 20 possesses a configurable polling interval that is configured by controller 24 at least partially based upon the parameter(s) sensed by sensor 22. Referring now to FIG. 3A, the polling interval is the time interval ($T_P$) in between consecutive sniff operations at which telemetry module 22 is activated for a short period of time ($T_A$) to detect whether a communication signal is being received from external device 28. In order to conserve power, telemetry module is only powered on to perform these sniff operations during the period of time ($T_A$) and maintained in low power or power off inactive "sleep" state at other times, unless actually powered up to perform wireless data telemetry between IMD 10 and external device 28.

Figure 3B:
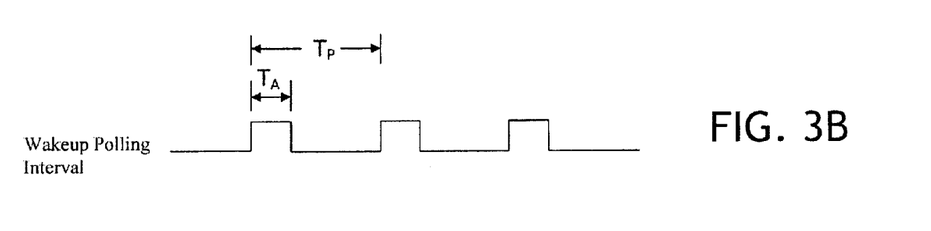

Under certain conditions, the polling interval ($T_P$) of telemetry module 20 can either be shortened or reduced in order to perform sniff operations more frequently, as shown by the shortened polling interval ($T_P$) of FIG. 3B as compared to the polling interval ($T_P$) shown in FIG. 5A. In one or more embodiments, the polling interval ($T_P$) is reduced in situations where IMD 10 is more likely to require telemetry communications. In certain circumstances, the polling interval ($T_P$) can be reduced to zero such that telemetry module 20 is immediately activated to perform sniff operations or other telemetry communications. For example, when sensor 22 senses parameters indicating an increase in activity in the patient, such as when the patient is waking up or when the patient is performing physical exercise, the polling interval ($T_P$) can be reduced as there may be a higher likelihood that IMD 10 will need to send or receive data from external device 28. Similarly, when the patient performs a patient-activating motion (e.g., tapping the sensor 22), the polling interval ($T_P$) can be reduced as the patient may be signaling that some action or communication by IMD 10 is desired by the patient.

Figure 3C:
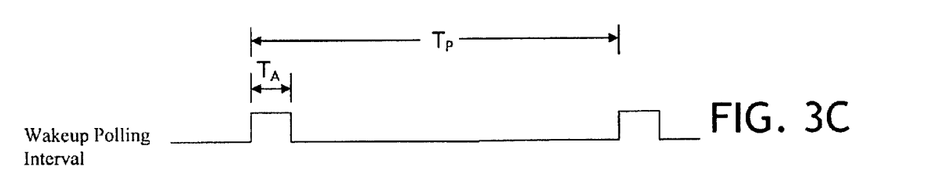

Under other conditions, the polling interval ($T_P$) of telemetry module 20 can either be lengthened or increased in order to perform sniff operations less frequently, as shown by the lengthened polling interval ($T_P$) of FIG. 5C as compared to the polling interval ($T_P$) shown in FIG. 5A. In one or more embodiments, the polling interval ($T_P$) is increased in situations where IMD 10 is more likely to not require telemetry communications, such as when sensor 22 senses parameters indicating a decrease in patient activity or when the patient is sleeping.

IMD 10 includes at least one sensor 22 configured to sense at least one parameter. In one embodiment, sensor 22 is a motion sensor that senses movement of IMD 10 or otherwise senses movement of a portion of the body 12 of the patient in which IMD 10 is implanted. In one embodiment, sensor 22 is configured to sense an activating motion such as a tapping motion imparted on sensor 22 by the patient, a physician or another individual. For example, sensor 22 may comprise an accelerometer, a piezoelectric sensor or other type of sensor capable of detecting patient-activating motions imparted on sensor 22. In one embodiment, sensor 22 may be configured to sense magnetic or inductive coupling or other near-field telemetry signals imparted on sensor 22 by an activating device positioned nearby sensor 22. In one embodiment, external device 28 may include a display and an input device that allows the patient or physician to selectively provide instructions or interact wirelessly with functionality of IMD 10 or another device. In one embodiment, sensor 22 is a patient activity sensor that senses activity by the patient, such as an increase in activity when the patient wakes up or a decrease in activity when a patient is going to sleep.

In one embodiment, sensor 22 is a position sensor that may be contained within the housing of IMD 10, e.g., within housing 14. As a position sensor, sensor 22 may comprise any sensor element capable of identifying positioning relative to the ground, i.e., the surface of the earth. In one example, sensor 22 formed as a position sensor may comprise a capsule-like housing that contains a mercury ball and various electrodes. The mercury ball can move in the capsule-like housing in response to the earth's gravitational forces. Movement of the mercury ball can cause the mercury ball to come into contact with one or more electrodes. Positioning of sensor 22, and thus positioning of IMD 10 can be determined based on which electrodes are in contact with the mercury ball inside the capsule-like housing. U.S. Pat. No. 4,846,195 describes one example of a position sensor that may be used, and is incorporated herein by reference in its entirety.

In one embodiment, sensor 22 is configured to sense a condition of the patient in which IMD 10 is implanted. For example, sensor 22 may comprise a heart sensor, such as the MDT Reveal® system, commercially available from Medtronic of Minneapolis, that is capable of sensing cardiac activity, electrocardiograms, heart rate, or the like. Reveal is a registered trademark of Medtronic, Inc. of Minneapolis, Minn.

Figure 4:
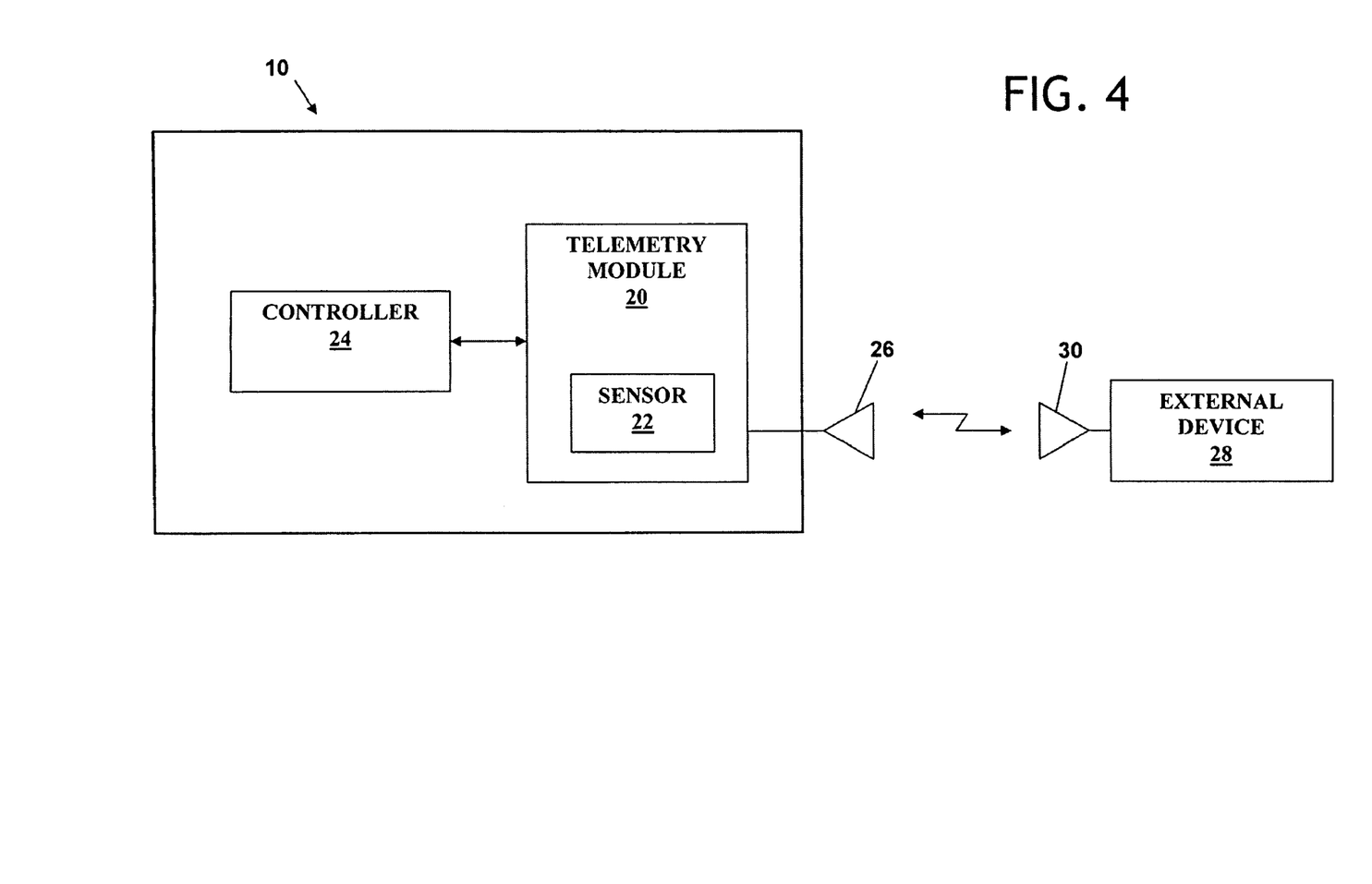
FIG. 4 is a block diagram illustrating the various components of another embodiment of an implantable medical device configured to operate in accordance with the present disclosure.
Figure 5:
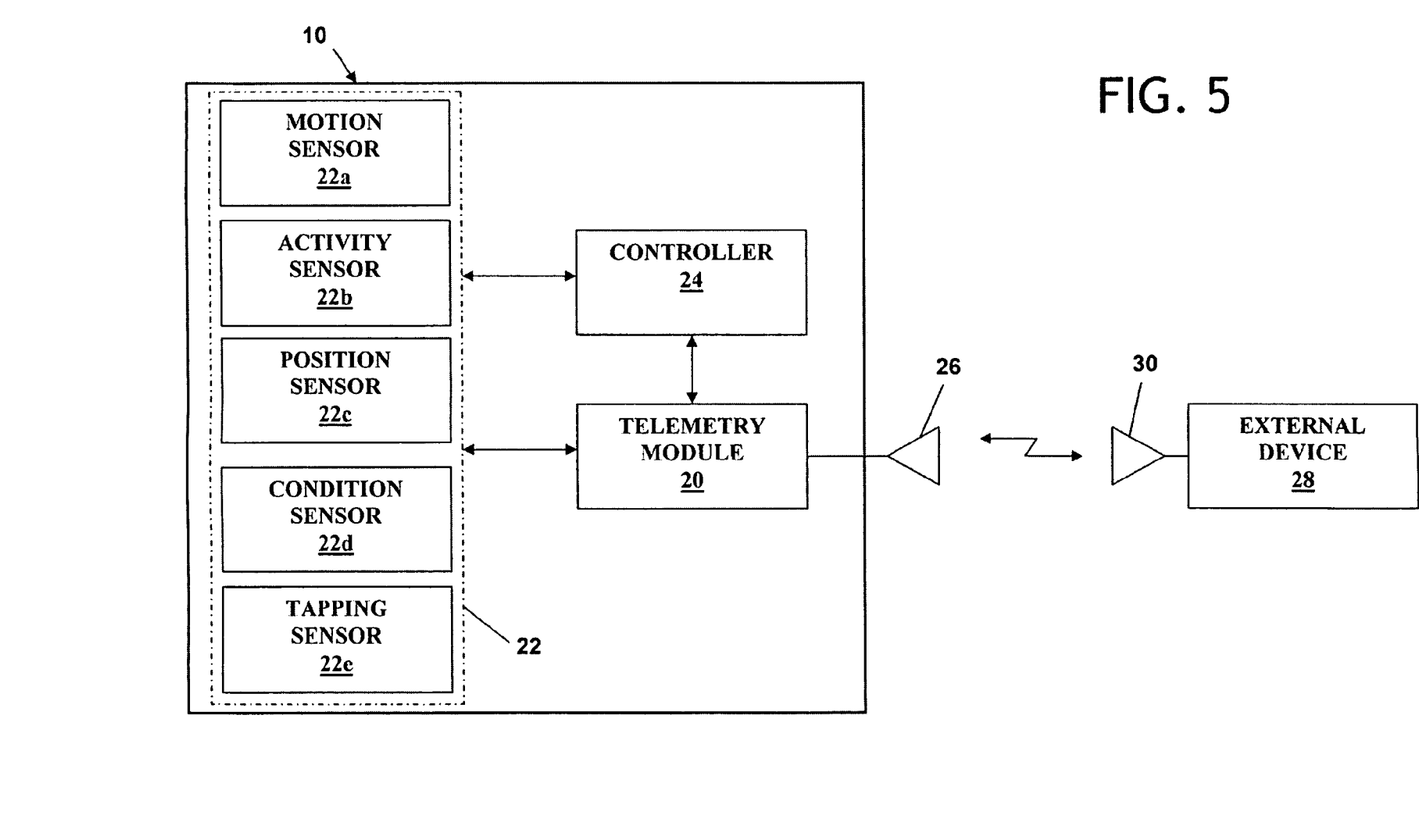
FIG. 5 is a block diagram illustrating the various components of a further embodiment of an implantable medical device configured to operate in accordance with the present disclosure.

In one embodiment, sensor 22 comprises a separate sensor positioned within the housing 14 of IMD 10 that is coupled to controller 24 to provide the sensed parameters to controller 24, as illustrated in FIG. 2. Sensor 22 may alternatively be located outside of housing 14 in order to facilitate certain types of sensed parameters, such as patient-activating tapping motions. In one embodiment, sensor 22 is incorporated within telemetry module 20, as shown in the block schematic illustration of FIG. 4. Any number or combination of different types of sensors 22 can be utilized to sense any number of parameters. For example, as illustrated in FIG. 5, sensor 22 may comprise motion sensor 22a, activity sensor 22b, position sensor 22c, condition sensor 22d, tapping sensor 22e or any other type of sensor or combination thereof.

In one or more embodiments, the polling interval ($T_P$) of telemetry module 20 is configured at least partially based upon the at least one parameter sensed by sensor 22. Referring now to the operational flow diagram of FIG. 6, telemetry module 20 is configured to operate in a low power or power off inactive mode (40) until telemetry module 20 is activated according to its initially set polling interval ($T_P$). In one embodiment, the initial polling interval ($T_P$) and/or the activation time ($T_A$) can initially be set or programmed to predetermined values. In certain embodiments, the polling interval ($T_P$) can be set or programmed such that the telemetry module 20 is maintained in a low power or power off "sleep" state until otherwise activated based on parameters sensed by sensor 22. In certain embodiments, the polling interval ($T_P$) can be set or programmed such that the telemetry module 20 is maintained in a power on "active" state until otherwise deactivated based on parameters sensed by sensor 22.

Figure 6:
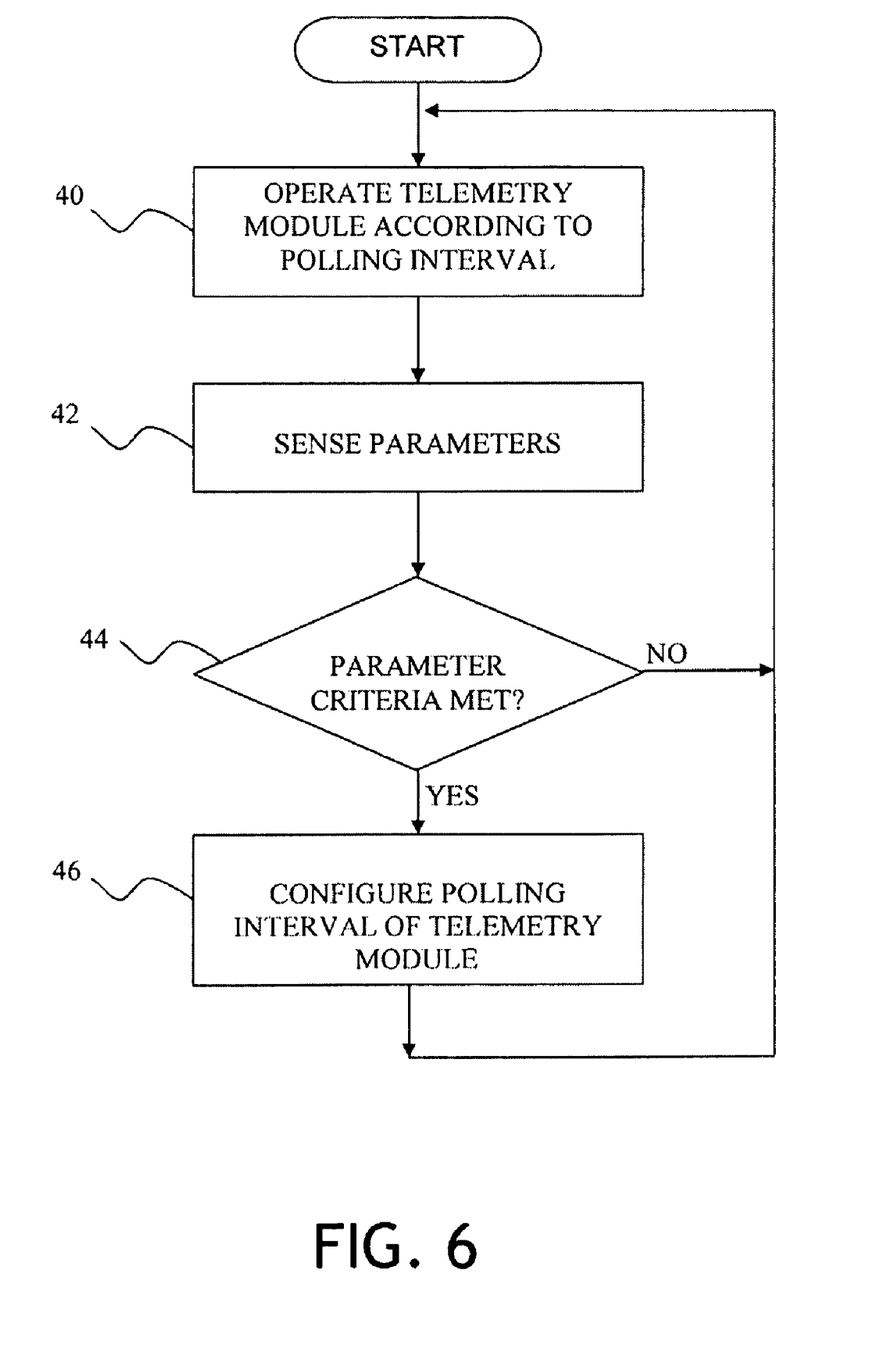
FIG. 6 is an operational flow diagram illustrating a process for configuring the polling interval of the telemetry module in accordance with one embodiment of the present disclosure.

Sensor 22 senses at least one parameter (42) and communicates the sensed parameter to controller 24. Controller 24 determines whether the sensed parameter (44) meets certain criteria. If the criteria are met, the polling interval ($T_P$) of telemetry module 20 is configured accordingly (46) by controller 24. Telemetry module 20 then operates (40) according to the newly configured polling interval ($T_P$) until the sensed parameters (42) dictate that the polling interval ($T_P$) should be configured to a different polling interval ($T_P$). In an alternative embodiment, telemetry module 20 can possess a standard polling interval ($T_P$) that is only temporarily configured to a different value for a temporary period of time, such that the polling interval ($T_P$) returns to the standard polling interval ($T_P$) upon expiration of the temporary period of time.

In one or more embodiments, controller 24 is configured to adjust the length of the polling interval ($T_P$) of telemetry module 20 when the at least one sensed parameter meets a certain criteria, wherein controller 24 is further configured to conversely adjust the length of the polling interval ($T_P$) of telemetry module 20 when the at least one sensed parameter fails to meet the certain criteria. In one or more embodiments, controller 24 is configured to reduce a length of the polling interval ($T_P$) of telemetry module 20 at a greater rate than the polling interval ($T_P$) is increased. If the patient, physician or any external device 28 desires to communicate with IMD 10, it is important that IMD 10 be accessible and be able to sense this desired communication. In order to facilitate this accessibility of IMD 10, telemetry module 20 is configured to have a shorter polling interval ($T_P$) to perform sniff operations or is configured to immediately perform sniff operations when the parameters sensed by sensor 22 meet certain criteria indicating the desirability of a shorter polling interval ($T_P$). For example, when IMD 10 includes a tapping sensor 22e, a patient or physician can indicate an immediate desire to perform telemetry between IMD 10 and external device 28 by tapping on the tapping sensor 22e. If a patient is visiting a physician's office or is having medical procedures performed at a hospital, IMD 10 can be activated or the polling interval ($T_P$) of telemetry module 20 can be made sufficiently short to allow substantially immediate telemetry communications. By way of further example, certain patient activities, motions, positions or conditions may be more likely to present a situation where information should be communicated between IMD 10 and external device 28, such as when a patient initially wakes up or is engaging in strenuous activity.

After the polling interval ($T_P$) is shortened, the polling interval ($T_P$) can then be gradually increased back to its normal value or another desired value at a rate that is less than the rate at which the polling interval ($T_P$) is shortened. By way of example only, if the normal polling interval ($T_P$) dictated that telemetry module 20 sniff for wake-up communication signals from external device 28 according a standard period (e.g., every 10 seconds), the polling interval ($T_P$) could immediately or rapidly be reduced to sniff for wake-up communication signals from external device 28 more frequently (e.g. every 5 seconds) if physical activity or motion or some other parameter were sensed. The polling interval ($T_P$) could also gradually be increased to sniff for wake-up communication signals from external device 28 less frequently (e.g., every 30 seconds) to conserve power if prolonged periods of inactivity or other conditions were sensed.

In one or more embodiments, an averaging function with a longer integration time for the sensed parameters can be utilized for increasing the polling interval ($T_P$) while using a shorter integration time for the sensed parameters for decreasing the polling interval ($T_P$). In this manner, if the polling interval ($T_P$) is long due to certain conditions (e.g., prolonged inactivity of the patient), IMD 10 requires only a small amount of a sensed parameter (e.g., a small amount of activity) to decrease the polling interval ($T_P$) to a reduced value to more frequently perform sniff operations. On the other hand, if the polling interval ($T_P$) is short (e.g., due to recent sensed activity of the patient), IMD 10 requires a longer amount of a sensed parameter (e.g., a longer amount of sensed inactivity) to increase the polling interval ($T_P$). This ensures that telemetry module 22 is activated quickly to perform sniff operations when so desired such that telemetry communications can occur between IMD 10 and external device 28 with minimal or no delay, whereas prolonged periods of time when criteria are not met by the sensed parameters (e.g., prolonged inactivity of the patient) are required to increase the polling interval ($T_P$).

By controlling the polling interval at which telemetry module 20 is activated to perform sniff operations based on certain parameters that are sensed by sensor 22, power consumption of IMD 10 can be conserved such that sniff operations are performed less frequently at times when telemetry communications are less likely to be required by IMD 10. Further, by reducing the polling interval ($T_P$) of telemetry module 20 at a greater rate than the rate at which the polling interval ($T_P$) is increased, the telemetry module 20 can be activated by sensed parameter to detect wake-up communication signals from external device 28 with minimal or no delay.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An implantable medical device comprising:
a sensor configured to sense at least one parameter;
a controller configured to receive data from the sensor; and
a telemetry module coupled to the controller for communication between the implantable medical device and an external device, the telemetry module having a configurable polling interval at which the telemetry module is activated for a period of time to detect whether a communication signal is being received from an external device, the polling interval of the telemetry module being configured at least partially based upon the at least one parameter sensed by the sensor, wherein the controller is configured with a first integration time for processing the sensed parameter to determine whether to reduce a length of the polling interval and a second integration time that is longer than the first integration time for processing the sensed parameter to determine whether to increase the length of the polling interval.

2. The implantable medical device of claim 1, wherein the sensed parameter is motion of a portion of a body of a patient, wherein the controller is configured to adjust the length of the polling interval of the telemetry module based upon the sensed patient motion.

3. The implantable medical device of claim 1, wherein the sensed parameter is a condition of a patient, wherein the controller is configured to adjust the length of the polling interval of the telemetry module based upon a relation of the sensed condition of the patient to a certain threshold.

4. The implantable medical device of claim 1, wherein the sensed parameter is a position of the implantable medical device relative to the earth and indicative of patient position, wherein the controller is configured to adjust the length of the polling interval of the telemetry module based upon the sensed position.

5. The implantable medical device of claim 1, wherein the telemetry module is configured to have the polling interval configured by the controller, wherein the controller is configured to receive instructions from an external device with which the telemetry module is capable of communicating in order to configure the polling interval.

6. The implantable medical device of claim 1, wherein the controller is configured to adjust the length of the polling interval of the telemetry module when the at least one sensed parameter meets a certain criteria and to conversely adjust the length of the polling interval of the telemetry module when the at least one sensed parameter fails to meet the certain criteria,
wherein the controller is configured to reduce the length of the polling interval of the telemetry module at a rate greater than a rate at which the polling interval is increased.

7. The medical device of claim 1, wherein the polling interval is reduced such that the telemetry module is activated more frequently when the sensed parameter indicates an increase in activity of the patient and the polling interval is increased such that the telemetry module is activated less frequently when the sensed parameter indicates a decrease in activity of the patient.

8. The medical device of claim 7, wherein the sensed parameter need indicate only a small increase in activity of the patient to cause the reduction in the polling interval and the sensed parameter need indicate prolonged inactivity of the patient to cause the increase in the polling interval.

9. A method comprising:
operating an implantable medical device including a telemetry module for communicating between the implantable medical device and an external device, the telemetry module having a polling interval at which the telemetry module is activated for a period of time to detect whether a communication signal is being received from the external device;
sensing at least one parameter;
configuring the polling interval of the telemetry module at least partially based upon the at least one parameter sensed, wherein the configuring the polling interval includes processing the sensed parameter with a first integration time to determine whether to reduce a length of the polling interval and processing the sensed parameter with a second integration time that is longer than the first integration time to determine whether to increase the length of the polling interval.

10. The method of claim 9, wherein
sensing the at least one parameter comprises sensing motion of a portion of a body of a patient, and
configuring the polling interval further comprises adjusting the length of the polling interval of the telemetry module based upon the sensed patient motion.

11. The method of claim 9, wherein
sensing the at least one parameter comprises sensing a condition of a patient, and
configuring the polling interval comprises adjusting the length of the polling interval of the telemetry module based upon a relation of the sensed condition of the patient to a certain threshold.

12. The method of claim 9, wherein
sensing the at least one parameter comprises sensing a position of the implantable medical device relative to the earth and indicative of patient position, and
configuring the polling interval comprises adjusting the length of the polling interval of the telemetry module based upon the sensed position.

13. The method of claim 9, further comprising receiving instructions from an external device with which the telemetry module is capable of communicating in order to configure the polling interval.

14. The method of claim 9, further comprising:
adjusting the length of the polling interval of the telemetry module when the at least one sensed parameter meets a certain criteria, and
conversely adjusting the length of the polling interval of the telemetry module when the at least one sensed parameter fails to meet the certain criteria,
wherein the length of the polling interval is reduced at a rate greater than a rate at which the polling interval is increased.

15. The method of claim 9, wherein configuring the polling interval of the telemetry module comprises at least one of:
reducing the polling interval such that the telemetry module is activated more frequently when the sensed parameter indicates an increase in activity of the patient; and
increasing the polling interval such that the telemetry module is activated less frequently when the sensed parameter indicates a decrease in activity of the patient.

16. The method of claim 15, wherein
reducing the polling interval comprises reducing the polling interval when the sensed parameter indicates only a small increase in activity of the patient; and
increasing the polling interval comprises increasing the polling interval when the sensed parameter indicates prolonged inactivity of the patient.

17. An implantable medical device comprising:
means for sensing at least one parameter;
means for controlling a telemetry module arranged for communicating between the implantable medical device and an external device, wherein the means for controlling a telemetry module configures a polling interval at which the telemetry module is activated for a period of time to detect whether a communication signal is being received from an external device, the polling interval of the telemetry module being configured at least partially based upon the at least one parameter sensed, wherein the configuring the polling interval includes processing the sensed parameter with a first integration time to determine whether to reduce a length of the polling interval and processing the sensed parameter with a second integration time that is longer than the first integration time to determine whether to increase the length of the polling interval.

18. The implantable medical device of claim 17, wherein the means for controlling a telemetry module adjusts the length of the polling interval of the telemetry module when the at least one sensed parameter meets a certain criteria and conversely adjusts the length of the polling interval of the telemetry module when the at least one sensed parameter fails to meet the certain criteria.

19. An implantable medical device comprising:
a sensor configured to sense at least one parameter;
a controller configured to receive data from the sensor representing the sensed parameter; and
a telemetry module coupled to the controller for communication between the implantable medical device and an external device, the telemetry module having a configurable polling interval at which the telemetry module is activated for a period of time to detect whether a communication signal is being received from an external device, a length of the polling interval of the telemetry module being configurable at least partially based upon the at least one parameter sensed by the sensor, wherein the controller is configured with a first integration time for processing the sensed parameter to determine whether to reduce a length of the polling interval and a second integration time that is longer than the first integration time for processing the sensed parameter to determine whether to increase the length of the polling interval.

* * * * *